United States Patent
Schulhauser et al.

(10) Patent No.: US 9,545,215 B2
(45) Date of Patent: Jan. 17, 2017

(54) APPARATUS AND METHOD FOR DETECTING CARDIAC EVENTS

(75) Inventors: Randal C. Schulhauser, Phoenix, AZ (US); John K. Day, Chandler, AZ (US); Scott Wayne Haskin, Mesa, AZ (US); Tho V. Huynh, Gilbert, AZ (US); Todd A. Kallmyer, Tempe, AZ (US); Brian Bruce Lee, Golden Valley, MN (US); Jeffrey O. York, Mesa, AZ (US); William Cope, Maricopa, AZ (US)

(73) Assignee: Medtronic, Inc., Minneapolis, MN (US)

( * ) Notice: Subject to any disclaimer, the term of this patent is extended or adjusted under 35 U.S.C. 154(b) by 2494 days.

(21) Appl. No.: 12/184,020

(22) Filed: Jul. 31, 2008

(65) Prior Publication Data
US 2010/0030034 A1    Feb. 4, 2010

(51) Int. Cl.
| | |
|---|---|
| A61B 5/0205 | (2006.01) |
| A61N 1/37 | (2006.01) |
| A61B 5/0452 | (2006.01) |
| A61B 5/145 | (2006.01) |
| A61B 5/00 | (2006.01) |
| A61B 5/021 | (2006.01) |
| A61B 5/024 | (2006.01) |
| A61B 5/08 | (2006.01) |
| A61B 5/11 | (2006.01) |
| A61B 7/00 | (2006.01) |

(52) U.S. Cl.
CPC ........... *A61B 5/0452* (2013.01); *A61B 5/0205* (2013.01); *A61B 5/14539* (2013.01); *A61B 5/4839* (2013.01); *A61B 5/021* (2013.01); *A61B 5/024* (2013.01); *A61B 5/02055* (2013.01); *A61B 5/0816* (2013.01); *A61B 5/11* (2013.01); *A61B 7/00* (2013.01); *A61N 1/37* (2013.01)

(58) Field of Classification Search
CPC ............................... A61B 5/0205; A61N 1/37
USPC ...................................... 607/17–18
See application file for complete search history.

(56) References Cited

U.S. PATENT DOCUMENTS

| | | | |
|---|---|---|---|
| 6,064,910 | A | 5/2000 | Andersson |
| 6,622,046 | B2 | 9/2003 | Fraley |
| 6,699,200 | B2 | 3/2004 | Cao |
| 6,869,404 | B2 | 3/2005 | Schulhauser |
| 7,035,684 | B2 | 4/2006 | Lee |
| 7,066,891 | B2 | 6/2006 | Stadler |
| 7,096,060 | B2 | 8/2006 | Arand |
| 2005/0131465 | A1 * | 6/2005 | Freeman et al. ............... 607/5 |
| 2006/0009811 | A1 * | 1/2006 | Sheldon et al. ............... 607/17 |
| 2007/0027371 | A1 * | 2/2007 | Benaron et al. ............. 600/310 |
| 2007/0150014 | A1 * | 6/2007 | Kramer et al. ............... 607/17 |
| 2008/0119749 | A1 * | 5/2008 | Haro et al. ................... 600/528 |
| 2008/0140000 | A1 * | 6/2008 | Shuros et al. ............. 604/96.01 |

\* cited by examiner

*Primary Examiner* — William Levicky

(57) ABSTRACT

A method and system which includes a minimally invasive, implantable device with a sensor configured for collecting electrical data associated with cardiac performance, a sensor configured for collecting mechanical data associated with cardiac performance, a sensor for collecting optical data associated with cardiac performance, a sensor for collecting biochemical data associated with cardiac performance, and a processor for deriving cardiac conditions and actuating an alarm upon identifying a cardiac event.

20 Claims, 6 Drawing Sheets

APPARATUS AND METHOD FOR DETECTING CARDIAC EVENTS

TECHNICAL FIELD

Apparatus and methods are provided that relate to medical devices for monitoring physiological conditions and, in some embodiments, to a minimally invasive implantable device for monitoring a physiological conditions and detecting the onset of a critical cardiac event such as a myocardial infarction.

BACKGROUND

Heart disease is the leading cause of death in the United States. A heart attack (also known as an acute myocardial infarction (AMI)) typically results from a thrombus that obstructs blood flow in one or more coronary arteries. AMI is a common and life-threatening complication of coronary heart disease. The extent of damage to the myocardium is strongly dependent upon the length of time prior to restoration of blood flow to the heart muscle.

Myocardial ischemia is an intermediate condition in coronary artery disease during which heart tissue fails to receive oxygen and other nutrients from the blood. It is typically provoked by physical activity or other causes of increased heart rate when there is coronary occlusion, that is, one or more of the coronary arteries are obstructed by atherosclerosis thus limiting the supply of blood to heart.

Patients will often experience chest discomfort (angina) when the heart muscle is experiencing ischemia. However, the ischemic episodes may also be without observable symptoms. The presence or absence of symptoms appears to be independent of the severity of the ischemia. According to the American Heart Association, millions of Americans may have silent ischemia. If even minor forms of ischemia remain untreated, affected heart tissue can eventually die, placing the patient at a high risk of having a heart attack with little or no warning. In fact, ischemia remains one of the most prevalent causes of morbidity and mortality in the developed world.

The electrocardiogram ("ECG") is an important tool for monitoring heart activity and diagnosing heart conditions. The ECG is a recording of the electrical activity of the heart. This electrical activity causes the heart to contract. The contraction in turn causes blood to be pumped throughout the body. This electrical activity is spontaneously generated. As the cells within the heart change from a negative potential to a positive potential (depolarization), the muscles within the heart contract. Conversely, when the cells change from a positive to a negative potential (repolarization), the muscles return to their noncontracted state. The periodic contraction of the heart causes the pumping action. This spontaneous electrical activity typically occurs about once a second.

Acute myocardial infarction and ischemia may be detected from a patient's ECG, for example, by noting an ST segment shift (i.e., voltage change) over a relatively short (less than 5 minutes) period of time. U.S. Pat. No. 6,128,526 to Stadler et al. describes one type of ischemia detector that observes variation in the ST segment to identify an ischemic condition. Other ischemia detection techniques have relied upon measures of heart activity, patient workload and other factors.

By itself, an ECG may not always be sufficient for diagnosis. There are cases where an ECG may reflect the normal electrical activity of the heart, yet there is no actual pumping of blood from the heart. This condition, known as pulseless electrical activity (PEA), can be discovered if tissue perfusion is not detected even though an ECG waveform is present. Furthermore, there are certain mechanical and/or chemical changes in body physiology which typically precede or coincide with changes in the electrical activity of the heart.

For example, seconds after a coronary occlusion the potassium ion (K+) and sodium ion (NA+) concentrations in and outside cardiac myocytes are disturbed. This chemical change results in muscle contraction and relaxation dysfunction, causing mechanical changes such as a rise in the filling pressure to compensate for reduced systolic pressure. Shortly after this mechanical change, corresponding electrical activity is indicated on an ECG.

Another mechanical measure relates to heart sounds. There are four audible sounds are generated during each heartbeat that have been used to assess heart performance and augment the diagnosis of heart conditions. These heart sounds are produced by blood turbulence and vibration of cardiac structures due primarily to the closing of the valves within the heart. These four sounds are identified as S1, S2, S3, and S4. S1 is usually the loudest heart sound and is the first heart sound during ventricular contraction. S1 occurs at the beginning of ventricular systole and relates to the closure of the atrioventricular valves between the atria and the ventricles. S2 occurs at the beginning of the diastole and relates to the closing of the semilunar valves separating the aorta and pulmonary artery from the left and right ventricles, respectively. S1 and S2 can be easily heard with a stethoscope ("normal heart sounds"). S3 and S4, however, can usually not be heard in the normal heart ("abnormal heart sounds") of a person over 40 years old. S3 occurs in the early diastolic period and is caused by the ventricular wall distending to the point it reaches its elastic limit. S4 occurs near the end of atrial contraction and is also caused by the ventricular wall distending until it reaches its elastic limit.

Heart sounds have also been used to assess the severity of important types of cardiac disease. For example, after age 40, S3 can indicate congestive heart failure, and S4 can indicate hypertension, acute myocardial infarction, or coronary artery disease.

Implantable cardiac devices, known as cardiac rhythm management devices (CRMs), that can treat heart problems are presently known and commercially available. CRMs include pacemakers (PMs) which utilize electrical impulses to regulate the beating of the heart, biventrical PMs also known as cardiac resynchronization devices (CRTs), implantable cardioverter defibrillators (ICD) for providing burst pacing pulses or a defibrillation shock to the heart when the heart is beating too fast or goes into fibrillation, and monitoring devices that use one or more physiologic sensors.

These implantable devices monitor many of the conditions that are indicative of cardiac events. However, symptoms are often highly varied. It is estimated that approximately one third of patients suffering from ischemia exhibit typical ischemic discomfort, while the remaining two thirds exhibit atypical symptoms or no symptoms at all. Similarly, classification of cardiac events is also varied. Thus, signs of trouble may be present but remain undetected by some of the common devices and detection methods for some time. Yet, it is well known that the benefits of treatment for heart conditions are greatest if administered as soon after the onset of a cardiac event as possible.

Present external automatic AMI monitoring approaches do not work well outside the hospital setting and cannot be worn for very long periods of time because of a number of factors, including the discomfort of external ECG electrodes and extensive maintenance required of these external lead systems since electrodes need to be replaced frequently leading also to poor compliance.

SUMMARY

Systems and methods are provided which, among other things, can monitor a plurality of physiological parameters relating to cardiac conditions and provide earlier detection of a cardiac event, such as an acute myocardial infarction or ischemia. In some embodiments, the systems and methods are minimally invasive, easily implemented once in place and provide accurate results, and can be carried out in a near-continuous manner so as to allow for chronic monitoring without disturbing the subject.

In some embodiments, systems and methods are provided which include a minimally invasive, implantable device including one or more sensors for ECG detection, heart sound detection and tissue perfusion activity detection. In some embodiments, systems and methods of detection are further refined by cardiac enzyme detection. The device may be configured to process the detected data, derive current cardiac conditions, identify if a cardiac event is occurring and notifying of any cardiac events requiring attention.

In some embodiments, a method for chronic monitoring of cardiac conditions incorporating an implantable medical device in a subject is disclosed which includes the steps of: collecting physiological data associated with the subject from the implantable device, wherein the collected data includes real-time electrocardial (or "electrocardiac") signal data, heart sound data, activity level data and tissue perfusion data; comparing the electrocardiac signal data with a threshold electrocardiac criteria for indicating a strong likelihood of a cardiac event; triggering an alarm state if the electrocardiac signal data is not within the threshold electrocardiac criteria; determining the current activity level of the subject from the activity level data if the electrocardiac signal data is within the threshold electrocardiac criteria; comparing the tissue perfusion data with a threshold tissue perfusion criteria for indicating a strong likelihood of a cardiac event if the current activity level is below a threshold activity level; triggering an alarm state if the threshold tissue perfusion data is not within the threshold tissue perfusion criteria; and triggering an alarm state if the threshold tissue perfusion data is within the threshold tissue perfusion criteria and the heart sound data indicates that S3 and S4 heart sounds are detected, wherein if an alarm state is not triggered the physiological data associated with the subject is collected at the expiration of a preset period of time.

In one aspect, the threshold electrocardiac criteria may relate to ST segment deviation from preset values, which may be established based on prior history regarding the subject.

In another aspect, the current activity level may be categorized as a state relating to physical exertion and/or body posture of the subject.

In some embodiments, the tissue perfusion data is compared with a threshold tissue perfusion criteria if the current activity level indicates the subject is engaged in a minimal amount of activity or at rest.

In one aspect, the threshold tissue perfusion criteria may relate to an acceptable level of oxygenation in the adjacent body tissue. The acceptable level of oxygenation may be determined based on a change in color of adjacent body tissue, and compared with accepted medical standards.

In some embodiments, the aforementioned methods may also include the steps of: collecting biomarker data relating to biochemical indicators of a cardiac event; and triggering an alarm state if the biochemical indicators are detected.

In some embodiments, the aforementioned methods may also include the steps of: collecting respiration data relating to the subject's respiration; comparing the respiration data with a threshold respiration criteria for indicating a strong likelihood of a cardiac event if the current activity level is below a threshold activity level; and triggering an alarm state if either the threshold tissue perfusion data is not within the threshold tissue perfusion criteria or the respiration data is not within the threshold respiration criteria.

In some embodiments, the aforementioned methods may also include the steps of: collecting systolic pressure data; and triggering an alarm state if the following conditions are met: the activity level is below a threshold activity level; the threshold tissue perfusion data is within the threshold tissue perfusion criteria, the heart sound data does not indicate that S3 and S4 heart sounds are detected and the systolic pressure data indicates a systolic pressure change greater than a threshold criteria for systolic pressure.

In some embodiments, one or more of the threshold values are adjusted based on the determined activity level.

In some embodiments, a system for chronic monitoring of cardiac conditions incorporating an implantable medical device in a subject is disclosed which is configured to perform the aforementioned methods.

In some embodiments, an implantable system for the chronic monitoring of cardiac conditions in a subject is disclosed which includes: a support housing; a sensor disposed in the support housing and configured for collecting electrical data associated with cardiac performance; a sensor disposed in the support housing and configured for collecting mechanical data associated with cardiac performance; a sensor disposed in the support housing and configured for collecting optical data associated with cardiac performance; a sensor disposed in the support housing and configured for collecting biochemical data associated with cardiac performance; and a processor disposed in the support housing, the processor being in communication with the sensors and configured for collecting and processing sensor data to assess cardiac conditions and actuate an alarm upon identifying a cardiac event.

In some embodiments, the sensor disposed in the support housing and configured for collecting electrical data associated with cardiac performance may include a sensor for monitoring electrocardiac signals.

In some embodiments, the sensor disposed in the support housing and configured for collecting mechanical data associated with cardiac performance may include a sensor configured for monitoring sounds made by the heart functioning.

In some embodiments, the sensor disposed in the support housing and configured for collecting optical data associated with cardiac performance may include a sensor configured for detecting tissue perfusion.

In some embodiments, the sensor disposed in the support housing and configured for collecting biochemical data associated with cardiac performance may include a sensor configured to detect the presence of one or more cardiac enzymes, such as potassium ions, sodium ions, troponin, brain natriuretic peptide and creatine kinase.

In some embodiments, the sensor disposed in the support housing and configured for collecting mechanical data associated with cardiac performance may include a sensor for detecting systolic pressure.

In some embodiments, a sensor may be disposed in the support housing and configured for collecting activity level data associated with the level of activity engaged in by the subject.

In some embodiments, the sensor disposed in the support housing and configured for collecting activity level data associated with the level of activity engaged in by the subject may also include an accelerometer for measuring the activity of the subject and a sensor configured for measuring the rate of respiration of the subject.

These and other aspects of the system and method of the subject invention will become more readily apparent to those having ordinary skill in the art from the following detailed description of the invention taken in conjunction with the drawings.

DESCRIPTION OF THE FIGURES

So that those having ordinary skill in the art to which embodiments of the invention pertain will more readily understand how to make and use the method and system of the present disclosure, embodiments thereof will be described in detail herein below with reference to the drawings, wherein.

DETAILED DESCRIPTION OF THE INVENTION

Advantages of the systems and methods provided will become more readily apparent to those having ordinary skill in the art from the following detailed description of certain preferred and exemplary embodiments taken in conjunction with the drawings, which are not intended to limit the scope of the invention.

Figure 1:
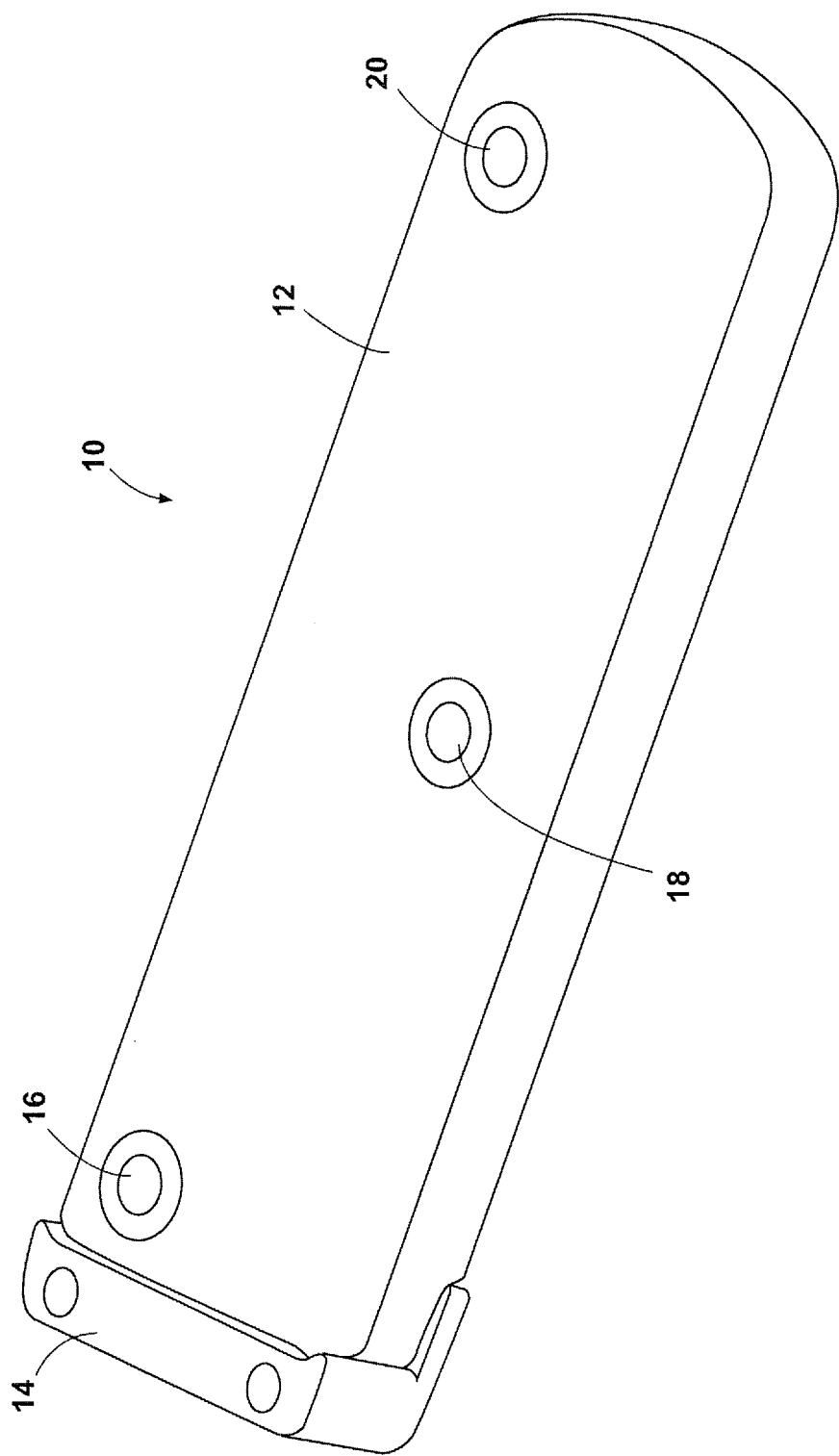
FIG. 1 is a perspective view illustrating one side of an exemplary implantable medical device constructed in accordance with some embodiments of the invention.
Figure 2:
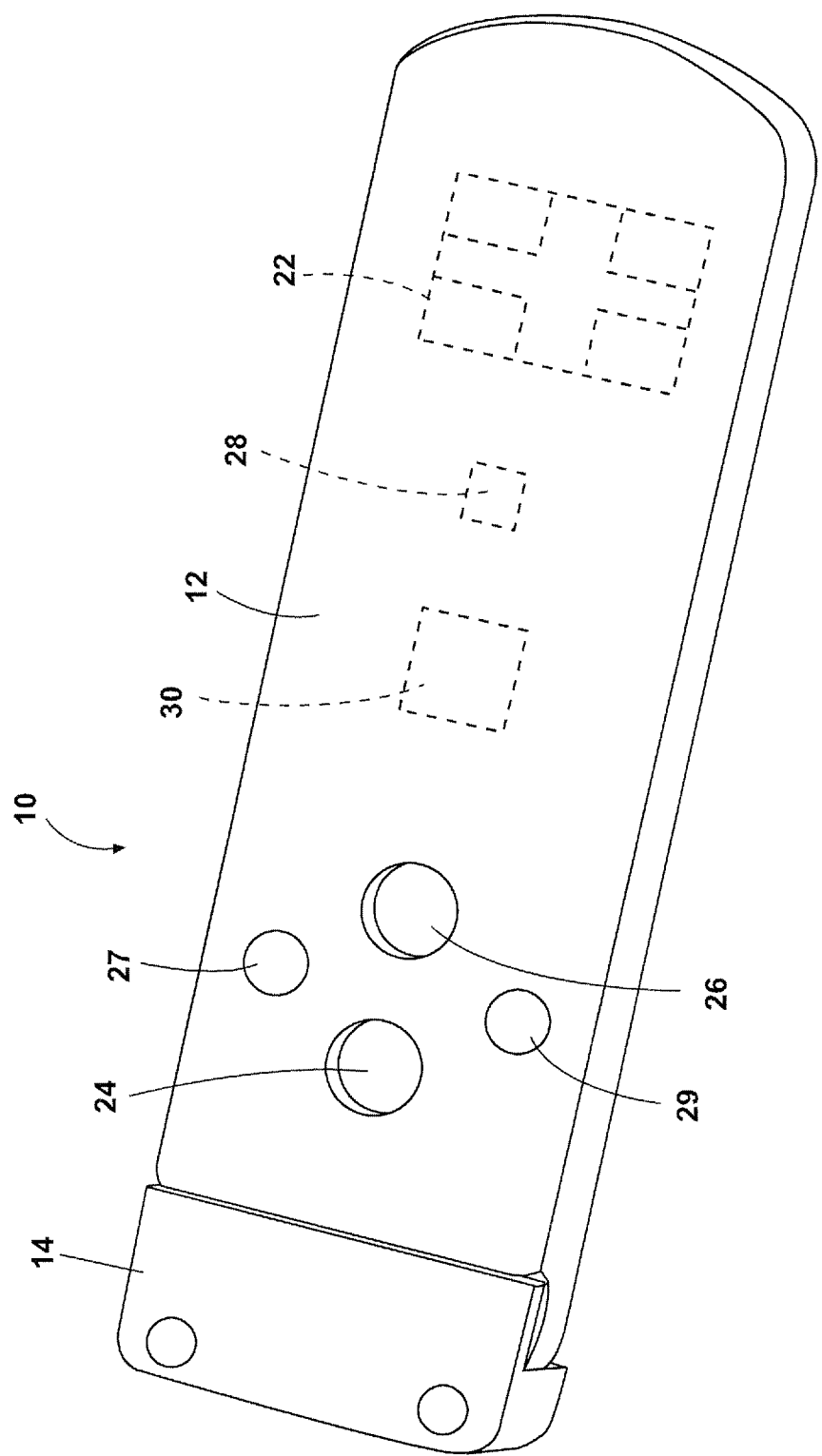
FIG. 2 is a perspective view illustrating another side of the exemplary implantable medical device shown in FIG. 1.

FIGS. 1 and 2 illustrate an implantable device 10 configured for monitoring physiological data relating to cardiac functioning and events in accordance with some embodiments of the invention. It should be understood that the invention is not limited to the size, shape and placement of components as shown in device 10. Rather, device 10 may be provided in a variety of forms, including devices generally disclosed in commonly assigned U.S. Pat. No. 5,987,352, issued to Klein, incorporated herein by reference in its entirety.

Device 10 is preferably implanted subcutaneously in the general thoracic region of a patient, but device 10 may otherwise be implanted in any location best suited for its intended application as described herein. For example, placement of device 10 near the sternum in the left pectoral region may generally provide good heart sound detection. However, it should be readily apparent that optimal device placement may vary between individuals. Thus, the optimal implant site for achieving the best performance of device 10 is likely to be determined on an individual basis by examination prior to implantation.

In some embodiments, device 10 is provided with a hermetically sealed housing or "can" 12 preferably formed from a biocompatible metal such as titanium and closed at one end by a plastic cap member 14. Cap member 14 may be formed of materials similar to those used for pacemaker connector blocks, such as polyurethane or epoxy. Cap member 14 may also include an antenna for facilitating communication between device 10 and other independent equipment, such as external monitoring or warning devices. An insulative coating, which may be formed from an insulating material such as a Parylene coating or other polymer, may be disposed on at least part of the surface of housing 12 and cap member 14. Housing 12 may also include a battery for powering the various components of device 10.

Device 10 in some embodiments is provided with three ECG sensing electrodes 16, 18 and 20 mounted to have an exposed side on the surface of housing 12. Electrodes 16, 18 and 20 can be configured for sensing a patient's subcutaneous ECG, among other things. One or more of electrodes 16, 18 and 20 may be formed from a biocompatible conductive metal such as platinum, iridium, titanium, or alloys thereof, and electrically connected to a conductive feed-through to an internal circuit board.

While the embodiment of device 10 is shown in FIGS. 1 and 2 having a particular shape and three ECG sensing electrodes, it is recognized that some embodiments of the invention may be practiced in an implantable device having more or less electrodes of the same or differing shapes and sizes. For example, multi-electrode ECG sensing in an implantable monitor is described in U.S. Pat. No. 5,313,953 issued to Yomtov, et al., incorporated herein by reference in its entirety. For example, Subcutaneous multi-electrode sensing system, method and pacer is described in U.S. Pat. No. 5,331,966 issued to Bennett et al., incorporated herein by reference in its entirety.

Device 10 is further provided with acoustical sensors within housing 12, such as heart sound sensor array 22 mounted in the embodiment of the invention shown herein. In one or more embodiments, heart sound sensor array 22 consists of four individual sensors which may be formed from a piezoelectric material, which may be a piezoelectric ceramic, film, or polymer. In one or more embodiments, heart sound sensor array 22 may consist of one or more sensors or can be provided as one or more miniaturized microphones. Sensor array 22 may also be mounted on housing 12 and hermetically sealed against body fluids. Sensor array 22 may be electrically coupled to a circuit board within device housing 12. Alternatively, sensor 22 may be mounted on or within cap member 14 and electrically coupled to an internal circuit board via feedthrough wires. Sensor array 22 is mounted on a diaphragm or other component that stabilizes the position of sensor 22 while providing good acoustical coupling. A monitor housing including a microphone diaphragm, which may be adapted for use with some embodiments of the invention, is generally disclosed in the above-cited U.S. Pat. No. 6,409,675, issued to Turcott, incorporated herein by reference in its entirety. Heart sound sensors which may be adapted for use with some embodiments of the invention, either by themselves or as part of array 22, are generally disclosed in U.S. Pat. No. 6,869,404, issued to Schulhauser et al., incorporated herein by reference in its entirety.

In one or more embodiments, device 10 further includes optical sensors 24 and 26 mounted to have an exposed side on housing 12 and configured for measuring tissue perfusion. Sensors 24 and 26 may be of any suitable type configured to determine the level of oxygenation of the surrounding tissue. For example, sensors 24 and 26 may use color or tonal changes to determine how oxygenated the tissues is, since the color of tissue varies when deprived of oxygen (e.g., from red to blue). Thus, sensors 24 and 26 may include one or more light-emitting diodes (LED) (or other light sources) and one or more photodetectors. Some sensors which may be adapted for use with some embodiments of the invention are generally disclosed in U.S. Pat. Pub. No. 2007/0156085, incorporated herein by reference in its entirety.

In one or more embodiments, device 10 further includes a diagnostic marker or "biomarker" sensor 27 configured to detect a cardiac enzyme or other biochemical indicators and/or other physiological changes which may be correlated to cardiac disorders. For example, sensor 27 may be configured to detect potassium ion concentration, sodium ion concentration, plasma atrial natriuretic peptide (ANP) and/or brain natriuretic peptide (BNP), troponin, glycogen phosporase, creatine kinase, or combinations thereof, as well as other biochemicals that can be used to indicate the onset of a cardiac event. Biomarker sensor 27 may employ single electron transistor detection technology.

In one or more embodiments, device 10 further includes an accelerometer 29 that provides information which allows device 10 to be adaptive or responsive to activity by the subject, as may be measured by the movement and/or position of the subject. The data provided by accelerometer 29 can therefore be used to adjust or correct the data received from other sensors in device 10 by considering the state of the patient (e.g., at rest, slightly active, moderately active or highly active, among others) when interpreting the remaining sensor data. For example, data obtained from sensors 16, 18, 20, 22, 24, 26 and 27 while the subject engaging in an activity, such as playing tennis, would likely be cause for alarm if the same data is received while the subject was watching television. Accelerometers for use in device 10 may include any type of motion sensor and/or a lead-based cardiac accelerometer that measures the strength of the cardiac contraction and the relative activity level of the subject.

Thus, in one or more embodiments, sensors 16, 18 and 20 provide electrical sensing data via ECG detection, sensor 22 provides mechanical sensing data measured by heart sound detection, sensors 24 and 26 provide optical or visual data based on perceived tissue perfusion within the subject, sensor 27 provides biochemical sensing data based on the relative presence of one or more biomarkers, and accelerometer 29 provides activity level data. Alternatively, systolic pressure and respiration may be measured by separate independent sensors not shown herein, such as through impedance measurements, or may be measured by one or more of the sensors discussed above (i.e., sensors 16, 18, 20, 22, 24, 26, 27 and 29), in combination with their already mentioned functionalities.

Housing 12 of device 10 may also include a processor 28, a digital memory 30, and other components as appropriate to affect the desired functionality of the device, such as analog to digital converters, signal amplifiers, and transceivers for communicating via an antenna as mentioned above. Processor 28 may be implemented with any type of microprocessor, digital signal processor, application specific integrated circuit (ASIC), field programmable gate array (FPGA) or other integrated or discrete logic circuitry programmed or otherwise configured to provide functionality as described herein. Processor 28 executes instructions stored in digital memory 30 to provide functionality as described herein. Instructions provided to processor 28 may be executed in any manner, using any data structures, architecture, programming language and/or other techniques. Digital memory 30 is any storage medium capable of maintaining digital data and instructions provided to processor 28 such as a static or dynamic random access memory (RAM), or any other electronic, magnetic, optical or other storage medium.

In operation, device 10 suitably obtains physiological data via electrodes 16, 18 and 20, sensors 22, 24, 26 and 27, accelerometer 29, and/or other sources, if applicable. The data is provided to processor 28, which suitably analyzes the data to monitor and identify cardiac conditions, such as an event of ischemia. Data is stored in memory 30, and an automated response or report regarding the data may be generated as appropriate. Upon detection of cardiac conditions and identification of a cardiac event, device 10 may be configured to activate an alarm.

Alternatively or in addition to alarm activation, device 10 may include components, such as a defibrillation coil or pacing electrode, which allows it to select and deliver an appropriate therapy or coordinate the delivery of the therapy through communication with another device. Optional therapies that may be applied in various embodiments may include drug delivery, electrical stimulation, neurostimulation, modifications in pacing rate, and/or the like. In addition, in the event the therapy involves electrical stimulation, the amplitude, frequency, or pulse width of stimulating current can be controlled according to the indicated degree of ischemia to achieve an optimum therapeutic effect. In a further embodiment, determination of the severity of ischemic tissue can be used to choose other types of therapy such as drug delivery, as well as types, dosages and durations of drug delivery.

Figure 3:
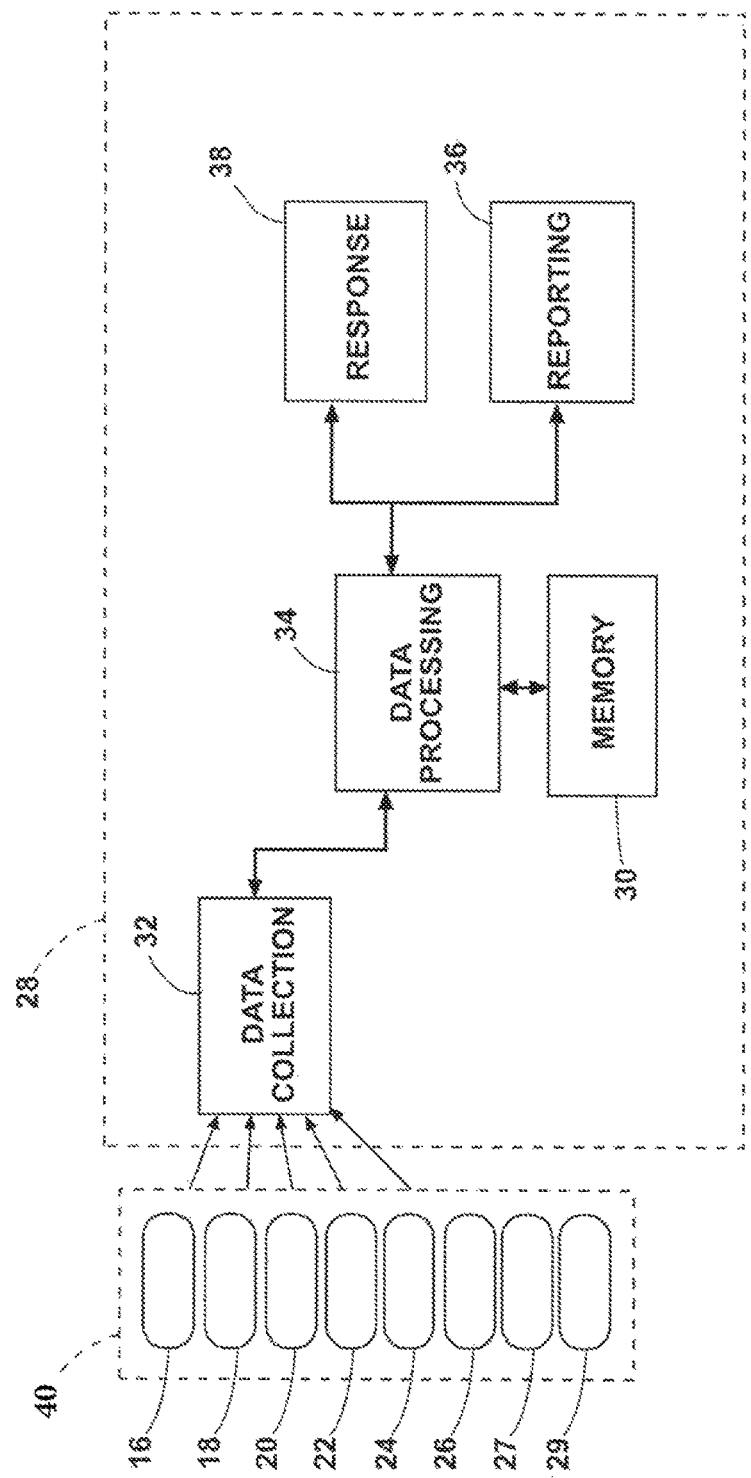
FIG. 3 is a conceptual block diagram of showing exemplary processing modules for an implantable medical device, such as the device shown in FIG. 1.

With reference now to FIG. 3, an exemplary data processing layout for a device 10 suitably includes a data collection module 32, a data processing module 34, and a reporting module 36 in accordance with one or more embodiments. Device 10 may also include a response module 38. Each of the various modules may be implemented with computer-executable instructions stored in memory 30 and executing on processor 28, or in any other manner. The exemplary modules and blocks shown in FIG. 3 are intended to illustrate one logical model for implementing an device 10, and should not be construed as limiting. Indeed, the various practical embodiments may have widely varying software modules, data structures, applications, processes and the like. As such, the various functions of each module may in practice be combined, augmented, optimized or organized in any other fashion.

Data collection module 32 suitably interacts with one or more data sources 40 to obtain data about the patient. In one or more embodiments, data sources 40 include electrodes 16, 18, 20 which provide electrical impulses or other observed signals that can be used to model the patient's electrocardiogram ("PQRST") waveform sensor 22 which provides information about heart sounds, sensors 24 and 26 which provide information about tissue perfusion, that is, the level of oxygenation in the body tissue, sensor 27 which provides information relating to biomarkers associated with cardiac conditions and disorders, and accelerometer 29 which provides information about the subject state of activity for qualifying the sensor data, or any combination thereof. Other sources of information about the patient's heart, blood, pressure, respiration, temperature or the like may also be provided by the aforementioned sensors or other sensors included in, or in communication with, device 10.

For example, other data sources collected by data collection module 32 may also include a blood pH sensor, a blood pressure monitor, or a sensor for determining cardiac conduction time. all of which may be incorporated in device 10 or independently of device 10 but otherwise in communication with data collection module 32. The various data sources 40 may be provided alone or in any combination with each other, and may vary widely from embodiment to embodiment. Sensors for cardiac conduction time and heart waveform data could be combined into a single pair of electrodes, for example. Moreover, other data sources 40 such as temperature sensors or the like could additionally or alternatively be provided.

Data collection module 32 suitably receives data from each of the data sources 40 by polling each of the sources 40, by responding to interrupts or other signals generated by the sources 40, by receiving data at regular time intervals, or according to any other temporal or on-demand scheme. Data may be received at data collection module 32 in digital or analog format according to any protocol. If any of the data sources generate analog data, data collection module 32 suitably translates the analog signals to digital equivalents using any form of analog-to-digital conversion scheme presently known or subsequently developed. Data collection module may also convert data from protocols used by data sources 40 to data formats acceptable to data processing module 34, as appropriate.

Data processing module 34 is any circuit, programming routine, application or other hardware/software module that is capable of processing data received from data collection module 32. In various embodiments, data processing module 34 is a software application executing on processor 28 to implement the process described herein. Accordingly, data processing module 34 suitably interprets received electrocardiac, heart sounds, tissue perfusion or other data to identify cardiac events, such as episodes of myocardial ischemia and to classify the severity of any event or ischemia observed.

By way of example and not of limitation, several systems and techniques for identifying and processing electrocardiac data to identify ischemia are described in U.S. Pat. Nos. 6,324,421; 6,381,493 and 6,397,100 which are all incorporated herein by reference, although any other techniques could be used in alternate embodiments. Ischemia can be detected, for example, when the patient's ST segment deviates from a baseline reading by more than a threshold amount, when the patient's cardiac conduction time exceeds a threshold value, or according to any other criteria. The baseline electrocardiac data (e.g. baseline ST segment deviation or cardiac conduction time) may be a static value, or may be updated over time. In various embodiments, the baseline data represents a mean or median electrocardiac value observed over any appropriate number of preceding samples. Threshold values may be any nominal values derived from a typical population of implant patients, or from any other source. Alternatively, the threshold values may be independently adjusted and set for a given patient as desired by the attending physician. For diagnosis purposes, the more recent values of ST segment deviation and/or conduction time, as well as other information, may be stored in a memory along with the most recent arrhythmia to facilitate diagnosis of any association between the onset of ischemia and arrhythmia episodes, for example. Heart sound signals sensed by sensor 22 can be calibrated and used to calculate blood pressure measurements, either through standard clinical method or as disclosed in the aforementioned U.S. Pat. No. 6,869,404, for example.

In an exemplary embodiment, processing module 34 receives data from data collection module 32 and interprets the data using conventional digital signal processing techniques. If, for example, an episode of ischemia is identified, data about the episode (e.g. the amount of ST segment deviation, duration of the episode, time and date of the episode, and/or the like) may be stored in memory. Alternatively or additionally, processing module 34 identifies episodes of ischemia from cardiac conduction time data or any other source(s) of data from data sources 40. Such information may also be stored within memory, which may correspond to hardware memory 30 or may be implemented with any other available digital storage device.

Data processing module 34 interprets collected data to gauge the severity of any condition, event or ischemia observed. Elevation of the ST segment, for example, commonly referred to as STEMI, typically indicates a very severe form of ischemia and likely indicates myocardial infarction. Depression of the ST segment indicates ischemia of lesser severity. When ST segment depression is observed, data from other sources 40 (e.g. heart sounds, tissue perfusion, etc.) can be checked to verify that an incident of ischemia is indeed occurring. Data from sources 40, and in particular accelerometer 29, can be used to determine if the patient is active or at rest during the ischemic period to aid in determining whether the episode is stable or unstable. Stable ischemic episodes may also be checked against historical data stored in memory to verify that the episode is consistent with prior episodes, and therefore does not warrant special attention.

After the severity of the particular episode is determined, processing module 34 may be configured to trigger an appropriate response as warranted by the severity of the episode. Responses are activated by sending a digital message in the form of a signal, passed parameter or the like to response module 38 and/or reporting module 36.

If a severe condition is not immediately detected, processing module 34 may be configured to process data from accelerometer 29 to provide context or qualify the interpretation of the other collected data. In some embodiments, data from accelerometer 29 is used as a "gatekeeper," that is, data processing module 34 analyzes the accelerometer information to determine the relative activity level or state of the subject, and then interprets the remaining collected data from sensors 16, 18, 20, 22, 24, 26 and 27 accordingly by automatically adjusting the expectations and threshold values relating thereto based on the determined state.

Reporting module 36 is any circuit or routine capable of receiving data from data sources 40 and producing appropriate feedback to the patient or to a physician. In various embodiments, suitable reports might include audible or visible alarms, wireless messages transmitted from a telemetry circuit via an antenna installed in device 10, or other data that may be downloaded from a serial, parallel or other interface. Reports for particular ischemic episodes may vary with the severity of the episode. Minor episodes may result in no alarm at all, or a relatively non-obtrusive visual or audible alarm. More severe episodes might result in a more noticeable alarm, in addition to an automatic response as described below.

The communication via a telemetry circuit may be a wireless, radio frequency message that provides data or indicates an ischemic condition and, in some embodiments, the severity of the ischemic condition. The external device that receives the wireless message may be a programmer/output device that advises a physician or other attendant of the ischemic condition, such as for example, via a display or a visible or audible alarm. Alternatively, the external device may be an interface to a telephone network such that device 10 is able to automatically notify emergency personnel if an extreme episode occurs.

Reporting module 36 may communicate via an interface, such as any serial, parallel or other interface to an external computing device. The interface and/or telemetry circuit may be used to provide information from device 10 to an external device. Information stored in memory 42 may be provided to an external computer or other device, for example, to aid in diagnosis or treatment of the patient.

Response module 38 may be any circuit, software application or other component that interacts with any type of therapy-providing system, which may include any type of therapy deliver mechanisms such as a drug delivery system, neurostimulation and/or electrocardial stimulation. In some embodiments, response module 38 may alternatively or additionally interact with an electrical stimulation therapy device integrated with device 10 to deliver pacing, post-extrasystolic potentiation, cardioversion and/or defibrillation therapy. Accordingly, the various responses to ischemic episodes that may be provided by device 10 vary from simple warnings to the patient to actual provision of therapy in various embodiments. Further, any therapy provided may be adjusted according to the severity of the particular episode. Drug dosage may be adjusted according to episode severity, for example, or pacing rates can be adjusted to respond to the severity of the particular episode.

The various components and processing modules of device 10 may be housed in a common housing such as that shown in FIGS. 1 and 2. Alternatively, portions of device 10 may be housed separately. For example, portions of a therapy delivery system could be integrated with device 10 or provided in a separate housing, particularly where the therapy delivery system includes drug delivery capabilities. In some embodiments, response module 38 may interact with a therapy delivery system via an electrical cable, wireless link or telemetry module.

In some embodiments, device processing system 28 is configured to obtain ECG data from sensors 16, 18 and 20 to determine whether the conditions for ST-Segment Elevation Myocardial Infarction or STEMI exist. If the conditions do not exist accelerometer 29 may be used to ascertain the level of activity of the subject before interpreting the remaining sensor data and triggering an alarm, response or both.

Figure 4:
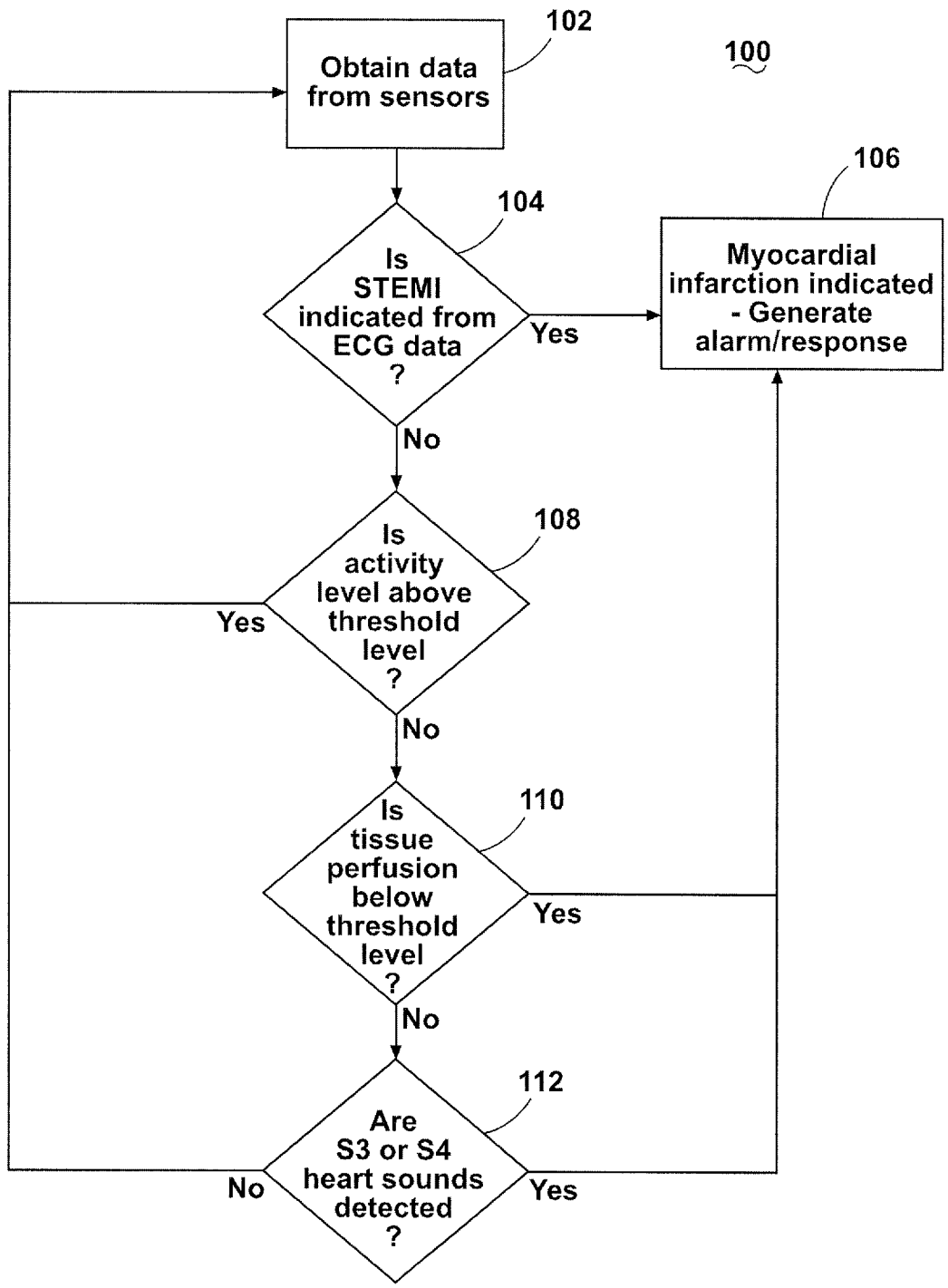
FIG. 4 is a flowchart of an exemplary process for assessing cardiac conditions and identifying the existence of cardiac events such as AMI and ischemia as executed within an implantable medical device such as the device shown in FIG. 1.

With reference now to FIG. 4, an exemplary process 100 is provided in accordance with one or more embodiments for collecting physiological data and assessing cardiac conditions suitably includes the broad steps of gathering data (i.e., step 102), processing the data to detect conditions such as AMI or ischemia (e.g., steps 104, 108, 110 and 112), and triggering an appropriate response (e.g., step 106). In various embodiments, the various steps of process 100 may be implemented with computer-executable instructions that are stored in a digital memory 30 and that are appropriately executed by processor 28.

Process 100 begins by obtaining data in step 102 at a data collection module 32 or other component operatively associated with device 10. Data may include electrocardiac information such as PQRST or ST waveform data, heart sounds, blood pressure, tissue perfusion, cardiac conduction times, accelerometer data, respiration data, systolic pressure, or the like. Data may be collected according to any scheme, but in an exemplary embodiment data measurements are taken at regular time intervals with a sufficiently high frequency to identify any episodes of AMI or ischemia occurring with in the patient (e.g., on the order every few minutes or seconds). After data is obtained, it may be formatted or otherwise processed as appropriate to put the data into a format that can be readily received and processed by data processing module 34 or another appropriate component in communication with data collection module 32.

In some embodiments, data from multiple sources is obtained and weighted with a scaling factor (i.e., a factor between 0 and 100%) to appropriately weigh the relative values of data obtained from the various sources. In such embodiments, ST segment deviation may be weighted higher than heart sounds, tissue perfusion or blood pH data, for example, during certain periods of observation. The relative weights assigned to the various factors may be programmable by a physician, and/or may vary according to time of day, level of patient exertion, amount of prior-diagnosed ischemia, or any other factors.

In one or more embodiments, serious conditions such as AMI are immediately identified in step 104. The collected data in step 102, particularly the data from ECG sensors 16, 18 and 20, may be analyzed to determine if the data differs with respect to baseline values by more than a threshold value, indicating STEMI and/or depressed ST-segment values. If threshold values are exceeded based on the ST segment data, myocardial infarction may be strongly indicated, and an appropriate response is triggered in step 106.

Alternatively, ischemia may also be indicated by ST segment depression. Generally speaking, ischemia can be presumed if an observed data value differs upon evaluation from a baseline by an amount that exceeds a threshold value. In the case of ST segment deviation, deviations on the order of about 1 mm or more may be indicative of ischemia, although other threshold values could be used in alternate embodiments. Thus, in an alternatively embodiment, an alarm response in step 106 may be triggered by any significant ST deviation from threshold values, either elevated or depressed.

An appropriate response to myocardial infarction might include sounding an audible alarm, automatically contacting emergency personnel, and/or administering any available therapies such as drug therapy, electrostimulation, or neurostimulation as appropriate, all of which may be incorporated within the purview of step 106.

Serious conditions may also be identified through merging and evaluating all data obtained from sources 40, even if ST-segment data derived from sensors 16, 18 and 20 do not immediately indicate cause for concern. Thus, process 100 continues to check for and identify episodes of AMI or ischemia as shown in the following steps.

In step 108, the relative activity level of the subject is determined. The activity level may be ascertained by analysis of the data received from accelerometer 29 in step 102, and the most likely posture or position of the subject (e.g., standing, reclining or sitting) at the time of data collection may also be ascertained from the data received from accelerometer 29. Alternatively, similar "posture" information may be received from an additional sensor or by analysis of data collected from another sensor associated with device 10. The relative amount of exertion of movement may be recorded and quantified as a value to be compared to a threshold activity level. A threshold activity level for purposes of comparison in step 108 may be preset according to the subject's history or other factors.

Figure 5:
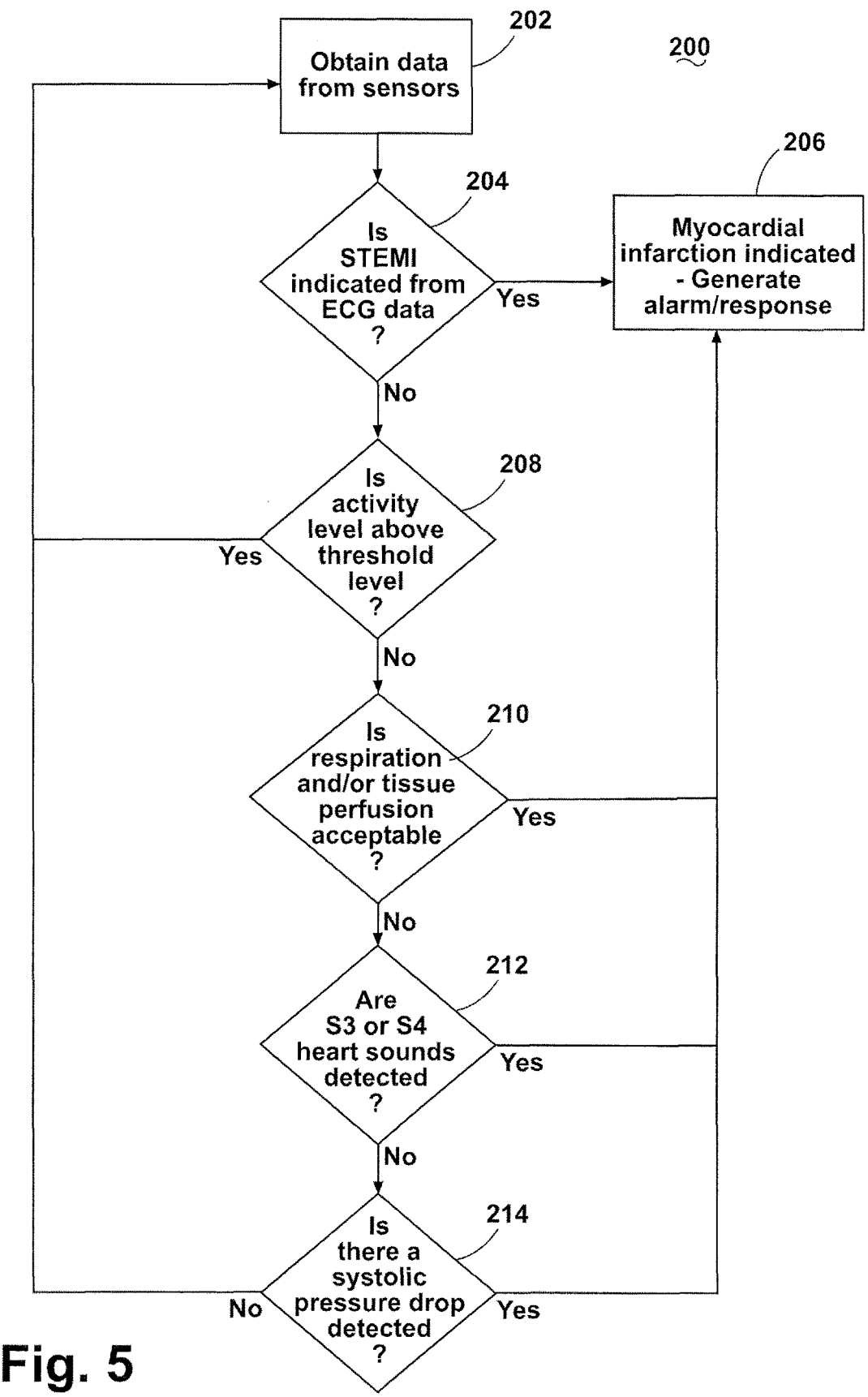
FIG. 5 is a flowchart of another exemplary process for assessing cardiac conditions and identifying the existence of cardiac events such as AMI and ischemia as executed within another embodiment of an implantable medical device such as the device shown in FIG. 1.

The activity level may be further delineated by data relating to the systolic pressure and respiration which may be received by existing sensors or added sensors, as further described in process 200 shown in FIG. 5. For example, ACC/AHA guidelines note that shortness of breath is a common myocardial infarction warning sign. Additionally, occlusion of coronary artery results in mechanical remodeling of the heart manifesting in a reduced systolic pressure. A sensor for systolic pressure detection may utilize the techniques disclosed in the aforementioned U.S. Pat. No. 6,869,404 incorporated herein.

If activity level data indicates that the subject is engaging in a level of activity above threshold values or the activity level otherwise justifies any unusual or non-conforming data obtained in step 102, cause for concern is not indicated and process 100 returns to step 102 or otherwise waits until the next data polling interval or triggering event.

If the patient is determined to be in a period of exertion in step 108, device 10 may continue to monitor the situation to ensure that the parameter return to within threshold levels after the patient returns to rest.

If there exists an ischemic episode while the patient is determined to be at rest in step 108, then unstable ischemia may be indicated, which is typically a medical emergency. Thus, if the ascertained activity level is within threshold values in step 108 or otherwise shown to be not responsible for any unusual data, then ischemia may still be possible and additional factors are evaluated to rule out or verify whether an ischemic condition exists that warrants alarm. In step 110, data from sensors 24 and 26 are used to indicate relative tissue perfusion, and whether current tissue perfusion is within threshold values. If tissue perfusion is below a threshold value (i.e., evidencing a reduced amount of oxygen in surrounding tissue) in step 110, ischemia and myocardial infarction may be indicated from this result and alarm and/or response is triggered in step 106.

If tissue perfusion is not below a threshold value in step 110, then process 100 considers other factors to verify or rule out alarm conditions. In step 112, heart sound sensor data from sensor 22 indicates whether S3 and/or S4 heart sounds are detected. If such sounds are detected in step 112, then an ischemic episode may be indicated and alarm and/or response is triggered in step 108. If such sounds are not detected in step 112, then cause for concern is not indicated and process 100 returns to step 102 or otherwise waits until the next data polling interval or triggering event.

In one or more embodiments, other information may be considered to correct the processing for other factors (e.g., physiological variants, etc.). Even if no ischemia is observed, processing may continue to consider additional factors and data, such as cardiac conduction rate, blood pH, heart rate, and the like, if appropriate, and as discussed in the same embodiments herein. In various embodiments, data may be stored within memory even if ischemia is not identified, and such data may be used to compute baseline values, to aid a physician in diagnosis or treatment, or for any other purpose.

If ischemia is indeed identified in step 104, then processing may continue to help determine the severity of the ischemic episode. Severity may be determined using any number of factors, such as the data obtained from monitoring heart sounds and tissue perfusion, and including whether the patient is active or at rest, whether the episode varies from prior episodes, the relative amount of affected tissue, the duration of the ischemic episode and the like.

Device 10 may also compare the most current data against threshold values based on stored data to verify that the ischemic episode is consistent with prior episodes in terms of severity, frequency, duration and/or the like. If the episode is consistent with prior data and resolves spontaneously when the patient is at rest, then the episode is deemed to be stable ischemia and an appropriate response can be generated. An alarm may be provided, for example, and data about the episode may be stored in memory for subsequent analysis.

As shown in FIG. 5, a process 200 is provided in accordance with one or more embodiments similar to process 100. Data collected in step 202 includes patient respiration rate, biomarker data relating to biochemical indicators of a cardiac event, and systolic pressure data, which may be obtained from data derived by existing sensors or additional sensors in device 10. In step 204, ECG sensor data is analyzed to determine if STEMI is discernable or if biomarkers are detected. If either STEMI conditions are indicated or one or more biomarkers are detected, alarm is triggered in step 206. If STEMI is not indicated and biomarkers are not detected, activity level is considered in step 208. If activity level is above threshold values, process 200 returns to step 202 to collect sensor data or wait for the next sensor polling results, presuming that if any non-conforming or unusual values exist, they are responsive to the elevated activity level and not a cardiac event.

If activity level is below threshold values or otherwise determined to be not responsible for any unusual values in step 208, the patient's respiration rate and tissue perfusion data are compared with threshold values in step 210.

If either the respiration or tissue perfusion is unacceptable, then the alarm and response are triggered in step 206. If the respiration and tissue perfusion data indicates acceptable values in step 210, then data relating to heart sounds is analyzed in step 212. If the S3 and/or S4 sounds have been detected in step 212, then the alarm and response are triggered in step 206. If the S3 and S4 sounds have not been detected in step 212, then the systolic pressure is analyzed to determine if there has been a drop below threshold values in step 214.

If the systolic pressure drop exceeds threshold values in step 214, then the alarm and response are triggered in step 206. If the systolic pressure is within threshold values in step 214, then process 200 returns to step 202 to collect sensor data or wait for the next sensor polling results.

It should be understood that the threshold values for tissue perfusion, respiration, heart sounds, systolic pressure, and any other cardiac condition parameters used to indicate cardiac events may be automatically adjusted to conform with the activity level detected, which provides data qualification and correction, thus enabling more accurate alarming and responsive measures.

Figure 6:
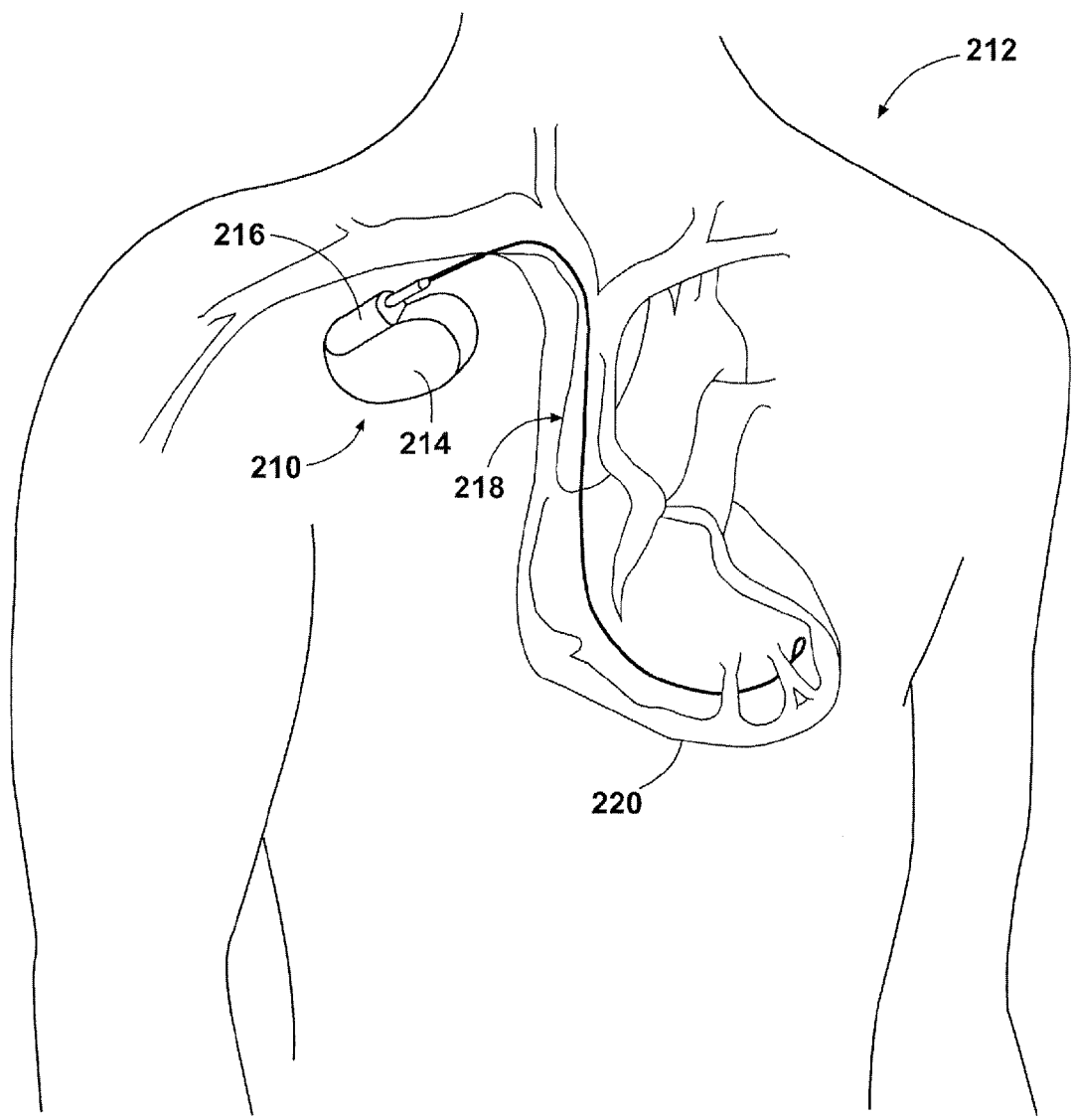
FIG. 6 illustrates an implantable medical device system in accordance with one or more embodiments implanted in a human body.

It should be understood that device 10 or features thereof may also be incorporated in other implantable devices, or external devices with implantable leads, and may include, for example, pacing electrodes and defibrillation coil electrodes in the event. In one or more embodiments, response module 38 may interact with an implantable medical device 210 implanted in a human body 212, as shown in the simplified schematic view of FIG. 6. Device 210 comprises a hermetically sealed enclosure 214 and connector module 216 for coupling device 210 to electrical leads 218 arranged within body 212 for delivery of therapy in the form of pacing pulses to a patient's heart 220. While device 210 is depicted in FIG. 5 as a separate component from device 10, it is understood that device 10 may be incorporated with device 210 in a single housing to provide the operative features discussed herein. Furthermore, device 210 or a combination of device 210 and device 10, may comprise any type of implanted device including for example, implantable cardioverter-defibrillators, combination pacemaker-cardioverter-defibrillators, implantable brain stimulators, implantable gastric system stimulators, implantable nerve stimulators or muscle stimulators, and implantable lower colon stimulators. In addition, devices in accordance with some embodiments of the invention may be configured to deliver pacing stimuli in a coordinated fashion to provide biventricular pacing, cardiac resynchronization or other benefits. Devices in accordance with some embodiments of the invention may also obtain input data from other internal or external sources (not shown) such as a blood pressure monitor, pH monitor, accelerometer or the like.

A minimally invasive implantable monitoring device has thus been described with an associated method for its operation. Embodiments described herein are considered exemplary and should not be taken as limiting with regard to the following claims. In the exemplary descriptions provided herein there are numerous specific details set forth in order to provide a more thorough understanding of some of the embodiments of the invention. It will be apparent, however, to an artisan of ordinary skill that other embodiments of the invention may be practiced without incorporating all aspects of the specific details described herein. Although the description herein is provided in sufficient detail for one skilled in the art to make, use and practice the invention, it should be understood that some specific features, quantities, sizes and/or measurements may have not been described in detail because, among other things, the invention should not be limited as such, and so as not to obscure the invention.

Moreover, the scope of the invention covers conventionally known manners for carrying out the described features and functions, as well as variations and modifications that may be made to the hardware or software components as would be understood by those skilled in the art now and hereafter. Numerous other changes may be made which will readily suggest themselves to those skilled in the art and which are encompassed in the spirit of this disclosure. It is to be understood that modifications and variations may be utilized without departure from the spirit and scope of systems and methods of the invention, as those skilled in the art will readily understand. Such modifications and variations are considered to be within the purview and scope of the appended claims and their equivalents.

The invention claimed is:

1. An implantable system for monitoring of cardiac conditions comprising:
   a plurality of sensors configured to collect physiological data associated with a subject of the implantable system at preset time intervals, wherein the collected physiological data includes real-time electrocardiac signal data, heart sound data, activity level data, and tissue perfusion data; and
   a processing circuitry configured to:
      compare the electrocardiac signal data with a threshold electrocardiac criteria for indicating a strong likelihood of a cardiac event;
      trigger an alarm state if the electrocardiac signal data is not within the threshold electrocardiac criteria;
      determine the current activity level of the subject from the activity level data if the electrocardiac signal data is within the threshold electrocardiac criteria;
      determine whether the current activity level is below a threshold activity level;
      compare the tissue perfusion data with a threshold tissue perfusion criteria for indicating a strong likelihood of a cardiac event if the current activity level is determined to be below a threshold activity level;
      trigger the alarm state if the threshold tissue perfusion data is not within the threshold tissue perfusion criteria; and
      trigger the alarm state if the threshold tissue perfusion data is within the threshold tissue perfusion criteria and the heart sound data indicates that S3 and S4 heart sounds are detected,
      wherein if the alarm state is not triggered, the processor collects the physiological data associated with the subject is at the expiration of the preset time interval.

2. The implantable system of claim 1, wherein the threshold electrocardiac criteria relates to ST segment deviation from preset values.

3. The implantable system of claim 1, wherein at least one of the plurality of sensors is configured to measure the current activity level as a state relating to at least one of physical exertion and body posture of the subject.

4. The implantable system of claim 1, wherein the threshold tissue perfusion criteria relates to an acceptable level of oxygenation in adjacent body tissue of the subject.

5. The implantable system of claim 4, wherein the acceptable level of oxygenation is determined based on the color of the adjacent body tissue of the subject.

6. The implantable system of claim 1, wherein at least one of the plurality of sensors is configured to measure biomarker data relating to biochemical indicators of a cardiac event, and wherein the processing circuitry is configured to trigger the alarm state if the biochemical indicators are detected.

7. The implantable system of claim 1, wherein the plurality of sensors is configured to:
   collect respiration data relating to the subject's respiration;
   wherein the processing circuitry is configured to compare the collected respiration data with a threshold respiration criteria for indicating a strong likelihood of a cardiac event in response to the current activity level being below a threshold activity level; and
   trigger the alarm state if the respiration data is not within the threshold respiration criteria.

8. The implantable system of claim 1, wherein the plurality of sensors is configured to collect systolic pressure data from the subject; and
   wherein the processing circuitry is configured to trigger the alarm state in response to the current activity level being below the threshold activity level, the threshold tissue perfusion data being within the threshold tissue perfusion criteria, the heart sound data not indicating that S3 and S4 heart sounds are detected, and the systolic pressure data indicating a systolic pressure change greater than a threshold criteria for systolic pressure.

9. The implantable system of claim 1, wherein the processing circuitry is configured to change one or more threshold values based on the determined current activity level of the subject.

10. A system for monitoring of cardiac conditions incorporating an implantable medical device in a subject, comprising:

means for collecting physiological data associated with the subject from the implantable device at preset time intervals, wherein the collected data includes real-time electrocardiac signal data, heart sound data, activity level data and tissue perfusion data;

means for comparing the electrocardiac signal data with a threshold electrocardiac criteria for indicating a strong likelihood of a cardiac event;

means for triggering an alarm state if the electrocardiac signal data is not within the threshold electrocardiac criteria;

means for determining the current activity level of the subject from the activity level data if the electrocardiac signal data is within the threshold electrocardiac criteria;

means for determining whether the current activity level is below a threshold activity level;

means for comparing the tissue perfusion data with a threshold tissue perfusion criteria for indicating a strong likelihood of a cardiac event if the current activity level is determined to be below a threshold activity level;

means for triggering an alarm state if the threshold tissue perfusion data is not within the threshold tissue perfusion criteria; and means for triggering an alarm state if the threshold tissue perfusion data is within the threshold tissue perfusion criteria and the heart sound data indicates that S3 and S4 heart sounds are detected, wherein if an alarm state is not triggered, means for collecting the physiological data associated with the subject is at the expiration of the preset time interval.

11. A method for monitoring of cardiac conditions incorporating an implantable medical device in a subject, the method comprising:

collecting physiological data associated with the subject from the implantable device at preset time intervals, wherein the collected data includes real-time electrocardiac signal data, heart sound data, activity level data, and tissue perfusion data;

comparing the electrocardiac signal data with a threshold electrocardiac criteria for indicating a strong likelihood of a cardiac event;

determining the electrocardiac signal is within the threshold electrocardiac criteria;

determining the current activity level of the subject from the activity level data in response to the electrocardiac signal data being within the threshold electrocardiac criteria;

determining the current activity level is below a threshold activity level;

comparing the tissue perfusion data with a threshold tissue perfusion criteria for indicating a strong likelihood of a cardiac event in response to the current activity level being determined to be below the threshold activity level;

triggering an alarm state if the threshold tissue perfusion data is not within the threshold tissue perfusion criteria; and triggering the alarm state if the threshold tissue perfusion data is within the threshold tissue perfusion criteria and the heart sound data indicates that S3 and S4 heart sounds are detected, wherein if the alarm state is not triggered, the physiological data associated with the subject is collected at the expiration of the preset time interval.

12. The method according to claim 11, wherein the threshold electrocardiac criteria relates to ST segment deviation from preset values.

13. The method according to claim 11, wherein the current activity level is measured as a state relating to at least one of physical exertion and body posture.

14. The method according to claim 11, wherein the comparing the tissue perfusion data with the threshold tissue perfusion criteria includes comparing the tissue perfusion data with a threshold tissue perfusion criteria for indicating a strong likelihood of a cardiac event if the current activity level indicates the subject is engaged in a minimal amount of activity.

15. The method according to claim 11, wherein the threshold tissue perfusion criteria relates to an acceptable level of oxygenation in adjacent body tissue.

16. The method according to claim 15, wherein the acceptable level of oxygenation is determined based on the color of the adjacent body tissue.

17. The method according to claim 11, further comprising:

collecting biomarker data relating to biochemical indicators of a cardiac event; and triggering the alarm state if the biochemical indicators are detected.

18. The method according to claim 11, further comprising:

collecting respiration data relating to the subject's respiration;

comparing the respiration data with a threshold respiration criteria for indicating a strong likelihood of a cardiac event in response to the current activity level being below a threshold activity level; and triggering the alarm state if the respiration data is not within the threshold respiration criteria.

19. The method according to claim 11, further comprising:

collecting systolic pressure data; and triggering the alarm state in response to the current activity level being below the threshold activity level, the threshold tissue perfusion data being within the threshold tissue perfusion criteria, the heart sound data not indicating that S3 and S4 heart sounds are detected, and the systolic pressure data indicating a systolic pressure change greater than a threshold criteria for systolic pressure.

20. The method of claim 11, wherein one or more threshold values are changed based on the determined current activity level of the subject.

* * * * *